(12) United States Patent
Zou

(10) Patent No.: US 8,165,264 B2
(45) Date of Patent: Apr. 24, 2012

(54) METHOD OF PRE-RECONSTRUCTION DECOMPOSITION FOR FAST KV-SWITCHING ACQUISITION IN DUAL ENERGY COMPUTED TOMOGRAPHY (CT)

(75) Inventor: Yu Zou, Naperville, IL (US)

(73) Assignees: Kabushiki Kaisha Toshiba, Tokyo (JP); Toshiba Medical Systems Corporation, Tochigi-Ken (JP)

( * ) Notice: Subject to any disclaimer, the term of this patent is extended or adjusted under 35 U.S.C. 154(b) by 437 days.

(21) Appl. No.: 12/361,280

(22) Filed: Jan. 28, 2009

(65) Prior Publication Data

US 2010/0189212 A1 Jul. 29, 2010

(51) Int. Cl.
*A61B 6/03* (2006.01)
(52) U.S. Cl. .......................................................... 378/5
(58) Field of Classification Search ................ 378/5
See application file for complete search history.

(56) References Cited

U.S. PATENT DOCUMENTS

| | | | |
|---|---|---|---|
| 2004/0102688 A1* | 5/2004 | Walker et al. | 600/407 |
| 2005/0082491 A1* | 4/2005 | Seppi et al. | 250/370.11 |
| 2009/0097611 A1* | 4/2009 | Nishide et al. | 378/5 |
| 2009/0180585 A1* | 7/2009 | Fujimoto et al. | 378/5 |

OTHER PUBLICATIONS

Zou et al., Analysis of Fast kV-switching in Dual Energy CT using a Pre-reconstruction Decomposition Technique, Feb. 18, 2008, SPIE, vol. 6913, pp. 691313-1 to 691313-12.*
Zou, Yu, and Silver, Michael D., "Analysis of Fast kV-switching in Dual Energy CT using a Pre-reconstruction Decomposition Technique", Medical Imaging 2008: Physics of Medical Imaging. Edited by Hsieh, Jiang; Samei, Ehsan. Proceedings of the SPIE, vol. 6913, pp. 691313-691313-12, Feb. 18, 2008.

* cited by examiner

*Primary Examiner* — Edward Glick
*Assistant Examiner* — John Corbett
(74) *Attorney, Agent, or Firm* — Knoble Yoshida & Dunleavy, LLC

(57) ABSTRACT

Fast kV-switching is a dual energy acquisition technique in computed tomography (CT) in which alternating views correspond to the low and high tube voltages. Its high temporal resolution and its suitability to a variety of source trajectories make it an attractive option for dual energy data acquisition. Its disadvantages include a one-view misregistration between the data for high and low voltages, the potentially poor spectrum separation due to the more-like a sine wave rather than the desired square wave in fast kV-switching, and the higher noise in the low voltage data because of the technical difficulty in swinging the tube current to counter the loss of x-ray production efficiency and loss of penetration at lower tube voltages. Despite the disadvantages, symmetric view matching according to the current invention substantially improves streaks and other artifacts due to the view misregistration, sufficient spectrum separation even in a sinusoidal waveform swinging between 80 kV and 135 kV, and contrast-to-noise for the simulated imaging task maximized at monochromatic energy of 75 keV.

16 Claims, 14 Drawing Sheets

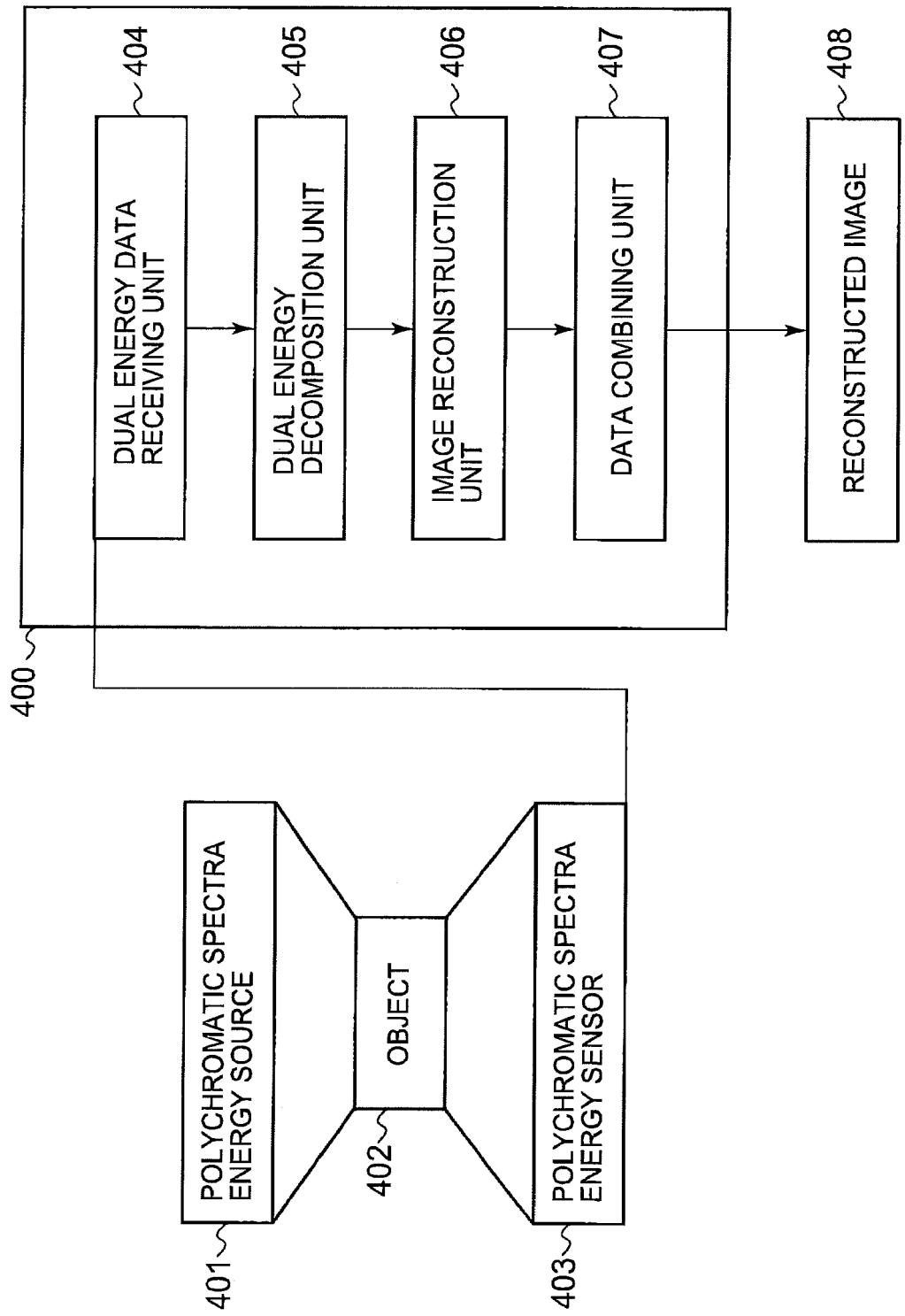

80 kVp data
Bow-tie filter
Noiseless
3600 TPPR
Air calibration
No attempt made to correct for polychromaticity.

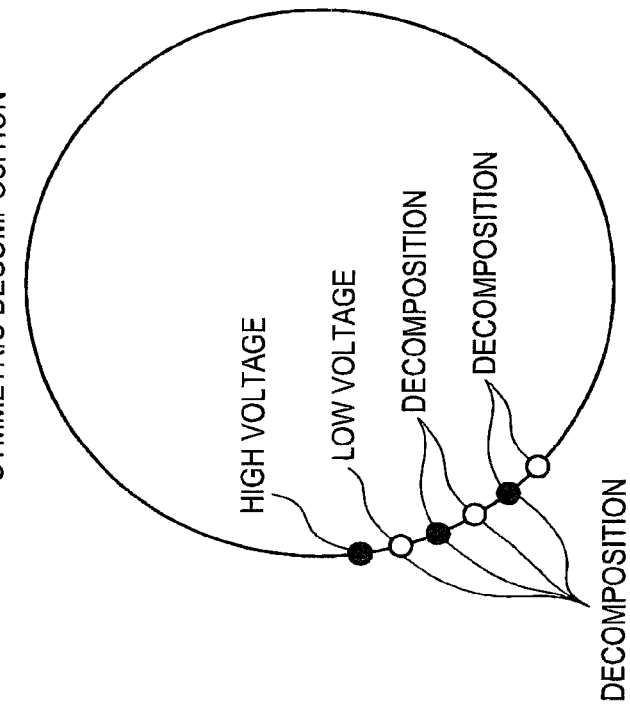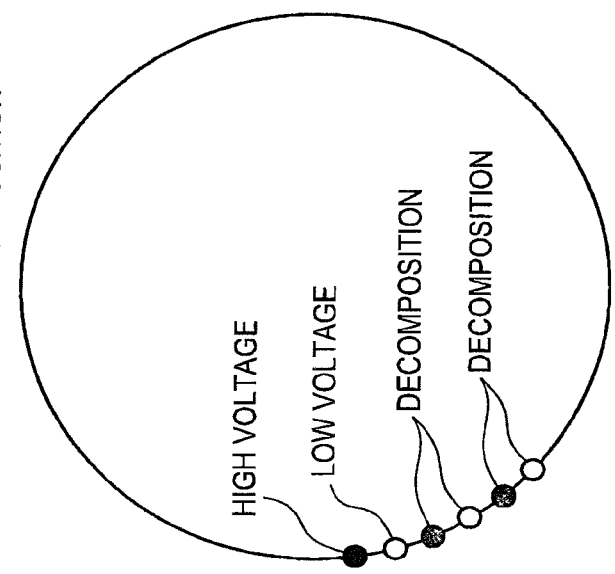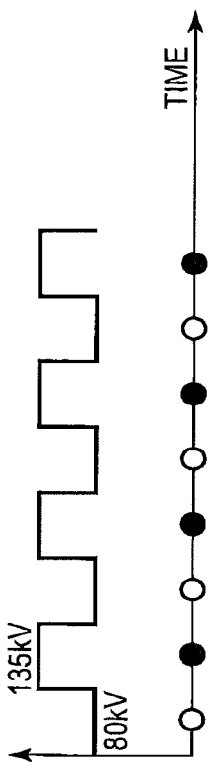

METHOD OF PRE-RECONSTRUCTION DECOMPOSITION FOR FAST KV-SWITCHING ACQUISITION IN DUAL ENERGY COMPUTED TOMOGRAPHY (CT)

FIELD OF THE INVENTION

Fast kV-switching techniques alternate voltages between projections (also called views) so that the odd (or even) projections correspond to the low (or high) tube voltage. The current invention is generally related to a method of pre-reconstruction decomposition for fast kV-switching acquisition in dual energy computed tomography (CT), and more particularly related to improved images that are substantially free from view misregistration and noise thanks to symmetric decomposition or view matching.

BACKGROUND OF THE INVENTION

Dual energy imaging in CT has been a promising technique since the first days of CT and was even mentioned in Godfrey Hounsfield's paper (1973) that introduced CT. The basic idea is to acquire two data sets at low and high energy levels and to use the pairs of the data sets to deduce additional information about the patient.

The physical basis of dual energy imaging includes two main mechanisms of the interaction of X rays with matter in the clinically relevant diagnostic energy-range from 30 keV to 140 keV, and the two interactions are photoelectric absorption and Compton scattering, each having its own functional dependence on x-ray energy. Photoelectric absorption is a rapidly decreasing function of energy while Compton scatter is a gentle function of energy. As shown in FIG. 1, the photoelectric interaction is a strong function of the atomic number of the absorbing tissue while scattering is nearly independent of Z. The physics enabled Alvarez and Macovski (1976) to develop a mathematical scheme, called dual-energy decomposition, to use the dual energy information.

In addition to the energy dependence, dual-energy decomposition must take X-ray sources into account. Since commercial clinical CT-scanners generally use polychromatic sources, the mathematics of dual energy imaging is not trivial. In this regard, single energy imaging with a polychromatic source does not have an exact and analytic solution. The current invention has the same above described physical bases but takes a somewhat different approach to the mathematics of dual-energy decomposition as will be described below. Assuming that:

| | |
|---|---|
| E | energy variable |
| H, L | labels for high and low energy spectra |
| l or l ($\beta, \gamma$) | integration path. This can be designated (in 2D CT) by a view and channel indices: $\beta, \gamma$ |
| I(l) | transmitted intensity along path l |
| $S_{H,L}(E, \gamma)$ | energy-weighted spectra where the channel index $\gamma$ is included to account for the bow-tie filter. |
| $\mu(E, x, y)$ | the energy-dependent linear attenuation coefficient of tissues at voxel x, y |
| $\mu_{1,2}^{H,L}$ | linear attenuation coefficient for basis material 1 or 2 averaged over the high (H)/low (L) spectra. |
| $\mu_{PE}(E)$, $\mu_{C\,i}(E)$ | the photoelectric and Compton linear attenuation coefficients of tissue i |
| $\mu_1(E), \mu_2(E)$ | the linear attenuation coefficients of known basis materials 1 and 2 |
| $g_{HL}(l)$ | projection datum with high or low spectra along path l |
| $c_{1\,2}(x, y)$ | how much the tissue at voxel x, y is like basis material 1 or 2 |

Instead of the polynomial approximation method introduced by Alverez and Moscovski with its known drawbacks, an approach combining a linear term with a non-linear beam hardening term was proposed previously. Because the linear term is dominant, an iterative solution to the dual energy data domain decomposition converges rapidly and is stable. To derive, the transmitted intensity is given by $$I(l) = \int S(E,\gamma) \exp[-\int_l \mu(E,x,y) dl] dE \tag{1}$$

The first key to dual energy CT is to realize that the attenuation coefficients are the sum of the physical processes. In the diagnostic energy range, the two dominant physical processes are photoelectric and Compton. Thus, the attenuation coefficient $\mu$ is expressed by the sum of $\mu_{PE}$ (photoelectric) and $\mu_C$ (Compton) as follows $$\mu(E,x,y) = \mu_{PE}(E,x,y) + \mu_C(E,x,y) \tag{2}$$

Factorize the energy and spatial dependencies of the linear attenuation coefficient $\mu$ and a sum over the spatially dependent pairs of $\mu_{PE}$ and $\mu_C$. Thus, Eqn. (2) is rewritten as:

$$\mu(E, x, y) = \sum_j \delta_{i, j(x,y)} (\mu_{PE,i}(E) + \mu_{C,i}(E)) \tag{3}$$

where the sum goes over all tissue types labeled by i. The interpretation of Eqn. (3) is that at a given location x,y, the tissue is type $$j, \delta_{i,j} = \begin{cases} 1 & \text{if } i = j \\ 0 & \text{if } i \neq j \end{cases}.$$

Replace the photoelectric and Compton by two known basis materials such as water and bone since one of which acts more like photoelectric (relatively high Z) and the other one acts more like Compton (relatively low Z):

$$\mu(E,x,y) \approx \mu_1(E)c_1(x,y) + \mu_2(E)c_2(x,y) \tag{4}$$

where $c_1(x,y)$ and $c_2(x,y)$ respectively represent how much the voxel at x,y is like basis material 1 and 2. This substitution is a good approximation as long as:

the K-edge of any tissue of interest is not in the energy range where the two spectra $S_{H,L}$ are not small and
the two basis coefficients have different enough energy dependence in the energy range of interest.

Even for a material whose K-edge is within this range such as iodine, the error may be small enough to be ignored.

It is very important that $\mu_1$ and $\mu_2$ have different energy dependencies. The energy dependence of photoelectric and Compton interactions is complicated functions of energy. But in the above specified diagnostic energy range, photoelectric goes approximately as $E^{-3}$ while Compton is fairly flat (obeying the Klein-Nishida formula). High Z materials are dominated by photoelectric (depending on the energy, about $Z^4$), while low Z materials are dominated by Compton as depicted in FIG. 1.

The linear attenuation coefficients for the basis coefficients are independent of location and are known. Next, Eqn. (4) is inserted into Eqn. (1). Since one equation has two unknowns, $c_1(x,y)$ and $c_2(x,y)$, two different spectra at high (H) and low (L) are needed to solve the two unknowns based upon the two equations. The result is:

$$I_H(l) = \int S_H(E,\gamma) \exp[-\mu_1(E)\int_l c_1(x,y)dl - \mu_2(E)\int_l c_2(x,y)dl] \, dE$$

$$I_L(l) = \int S_L(E,\gamma) \exp[-\mu_1(E)\int_l c_1(x,y)dl - \mu_2(E)\int_l c_2(x,y)dl] \, dE \quad (5)$$

Notice that the linear attenuation coefficients have been removed from the line path integrals. Now the projection data will be formed in the usual way by taking the logs:

$$g_H(l) = -\ln\int S_H(E,\gamma) \exp[-\mu_1(E)L_1(l) - \mu_2(E)L_2(l)] dE$$

$$g_L(l) = -\ln\int S_L(E,\gamma) \exp[-\mu_1(E)L_2(l) - \mu_2(E)L_2(l)] dE \quad (6)$$

where the following notation has been introduced:

$$L_{1,2}(l) = \int_l c_{1,2}(x,y) dl \quad (7)$$

The intermediate goal of the dual energy is to solve the two equations in (6) for $L_{1,2}$ and then to reconstruct $c_{1,2}(x,y)$ by standard CT reconstruction techniques. The solution for $L_{1,2}$ is discussed elsewhere including a pending patent application Ser. No. 12/106,907 filed on Apr. 21, 2008 and a reference entitled as "Analysis of Fast kV-switching in Dual Energy CT using a Pre-reconstruction Decomposition Technique," by Yu Zou and Michael D. Silver (2009). These references are incorporated into the current application by external reference to supplement the specification. Thus, an iterative solution to the dual energy data domain decomposition converges rapidly and is stable because of a dominant linear term with a non-linear beam hardening term so as to derive the transmitted intensity.

Despite the above described dual-energy decomposition, the clinical significance of dual-energy imaging may still remain a matter of controversy. Among other x-ray means, no researcher has identified a single significant application of clinical importance that is unique to dual-energy CT. On the other hand, currently installed dual-energy CT systems have uncovered some areas of clinical significance in relation to the dual energy imaging technique. In spite of the lack of an indispensable killer application, the potentially significant clinical applications of the dual-energy CT include: 1) the improved images that are free of beam-hardening at a range of monochromatic energies with enhanced contrast among some tissue types; 2) the identification of the chemical composition in tissues, which may be also useful in explosive detection in scanned luggage, 3) more quantitative, accurate and precise data such as in detecting an early bio-marker for therapy progression assessment, analyzing bone mineral and assessing the fat content in liver for suitability for organ transplant; 4) automatic subtraction of a tissue type such as bone subtraction (predominately a photoelectric absorbing material) from soft tissue (predominately a scattering material), or iodine contrast from bone; and 5) attenuation correction in nuclear medicine.

Regardless of the clinical significance, several hurdles remain for successful dual energy imaging. Most importantly, for image quality, the temporal and spatial registrations must be sufficiently accurate for the high and low energy data sets. The image processing is performed on the high/low ray-sum pairs, and each pair should ideally represent the same path through the patient at the same time. Another important image quality issue is related to the different dose and noise levels between the two data sets. Depending on how the dual energy is achieved, the low energy data set could be very noisy compared with the high energy data set because x-ray tubes are less efficient at lower voltages and the lower energy X rays usually have worse penetration in tissues, which will be a problem for larger patients. Lastly, yet another significant hurdle is how to obtain the dual energy data sets in a cost effective manner.

In the past two years, prior art attempts have implemented certain dual energy CT systems. For example, Siemens has installed a number of dual source CT-scanners, which is equipped with two X-ray sources, and each runs at a different energy level for generating the two data sets. Another example is that Philips at their Haifa research facility has developed a sandwich detector where the upper layer records the low energy data and the lower layer records the high energy data. A prototype system is installed at the Hadassah Jerusalem Hospital. In this regard, GE has developed a specialized detector using garnet for capture 2496 total projections per rotation (TPPR) at a high speed. Another method is called slow kV-switching, which scans the same region of the patient twice. For example, for a circular scan, the first rotation is at high kV, and the tube voltage is then switched to low kV before or during the next rotation. In this regard, slow kV-switching is about a factor of 1000 to 2000 slower than fast kV-switching.

TABLE 1 below summarizes advantages and disadvantages of selected ways to acquire dual energy data sets. Fast kV-switching techniques change voltages between projections (also called views) so that the odd and even projections respectively correspond to the low or high tube voltage. Among these prior art approaches, the fast kV-switching appears an attractive technique for dual energy acquisition for a number of reasons. Since the dual source CT-scanners and the sandwich detector CT-scanners respectively require additional costs for the dual X-ray sources and the sandwich detectors, they may not be cost-effective to obtain dual energy data sets. Similarly, although GE's detector for fast kV-switching energy CT is not summarized in TABLE 1, the semi-precious gem detector also incurs additional costs. In addition, both the dual source CT-scanners and the sandwich detector CT-scanners must resolve other technical difficulties that are associated with these systems as listed in the table below. On the other hand, although the slow kV-switching does not require additional parts or equipment, dual energy data sets result in poor temporal registration that is off by at least one rotation period as well as poor spatial registration in particular from helical scans. For these reasons, the prior art technologies remain to find a cost effective system and method to utilized the dual energy data for CT.

TABLE 1

| Options | Advantages | Disadvantages |
|---|---|---|
| Fast kV-switching (alternating views) | Temporal and spatial registration very good. Data domain methods possible leading to better IQ and flexibility. Helical acquisition no problem. | Limited energy separation unless square-wave waveform developed. Difficult to equalize dose/noise between high/low data sets. Development time and cost for fast, switching HVPS. |
| Slow kV-switching (alternating rotations) | Good energy separation. Easy to equalize dose/noise | Poor temporal registration; off by at least one rotation period. |

TABLE 1-continued

| Options | Advantages | Disadvantages |
|---|---|---|
| | between high/low data sets. Little equipment development necessary. Little or no added H/W costs. | Poor spatial registration, especially if doing helical scans and thus limited to image domain methods. Helical scans may require lower pitch and thus more dose. |
| Dual source | Good energy separation. Easy to equalize dose/noise between high/low data sets. | Temporal registration off by ¼ of the rotation period. Spatial registration requires tube alignment. Cost of two imaging chains. Field-of-view for dual energy limited by the smaller of the two imaging chains. Cross-scatter contamination. |
| Sandwich detector | Perfect temporal and spatial registration. Data domain decomposition methods valid. Helical acquisition no problem. | Limited energy separation. Cost and development of the detector. |

As illustrated in FIG. 2A, the fast kV-switching technique alternately changes voltages between projections (also called views) so that the odd and even projections correspond to either the low or high tube voltage as the X-ray tube moves in a direction as indicated by an arrow Although the switching X-ray ideally should have square waveforms, the X-ray may be closer to a sinusoidal waveform in reality as illustrated in FIG. 2B. In the current invention, square-wave and sinusoidal waveforms have been compared for fast kV-switching in resultant image quality and the dual energy decomposition. Please note that square-wave is the same as slow kV-switching if we ignore registration problems.

As already shown in TABLE 1, prior art fast kV-switching techniques without the use of dual sources or special detectors nonetheless have both advantages and disadvantages in acquiring dual energy data sets. The prior art fast kV-switching techniques have very good temporal and spatial registrations between corresponding high and low energy projections, which make data domain methods possible and lead to better IQ and flexibility. In addition, prior art fast kV-switching techniques acquire good dual energy data sets also through helical projections.

A disadvantage is the one view misregistration between corresponding high and low energy projections. Another problem is the difficulty of high noise in the low energy data because it may be technically difficult to swing the mA as fast as the kV. The current invention addresses these issues through a series of numerical simulation studies for improvement without necessarily involving the prior art solutions such as dual energy sources, specialized detectors or slow switching. A preferred embodiment will be described for fast kV-switching, spectra generation, and polychromatic data generation.

With respect to the current application, dual energy decomposition takes place in the data domain (before reconstruction) because of its greater flexibility compared with image domain (after reconstruction) decomposition. Therefore, the current invention will assume a data domain decomposition approach.

SUMMARY OF THE INVENTION

In order to solve the above and other problems, according to a first aspect of the current invention, a method of processing pre-reconstruction decomposition for fast kv-switching acquisition in dual energy computed tomography (CT), includes the steps of: fast switching an X ray tube between a predetermined high energy level and a predetermined low energy level; acquiring dual energy data sets at a predetermined total number of projections per rotation (TPPR); symmetrically matching the dual energy data sets into symmetrically matched pairs of the dual energy data sets; performing pre-reconstruction decomposition on the symmetrically matched pairs of the dual energy data sets to generate a dual energy computed tomography; and displaying the dual energy computed tomography.

According to a second aspect of the current invention, a method of processing pre-reconstruction decomposition for fast kv-switching acquisition in dual energy computed tomography (CT), includes the steps of: fast switching an X ray tube between a predetermined high energy level and a predetermined low energy level; acquiring dual energy data sets at substantially 900 total number of projections per rotation (TPPR); symmetrically matching the dual energy data sets into symmetrically matched pairs of the dual energy data sets; performing pre-reconstruction decomposition on the symmetrically matched pairs of the dual energy data sets to generate a dual energy computed tomography; and displaying the dual energy computed tomography.

According to a third aspect of the current invention, A dual energy computed tomography (CT) system for performing pre-reconstruction decomposition on dual energy data for fast kv-switching acquisition, includes: fast switching acquisition device for alternating an energy level at an X ray tube between a predetermined high level and a predetermined low level and for acquiring dual energy data sets at a predetermined total number of projections per rotation (TPPR); a dual energy decomposition unit operationally connected to the fast switching acquisition device for symmetrically matching the dual energy data sets into symmetrically matched pairs of the dual energy data sets and performing pre-reconstruction decomposition on the symmetrically matched pairs of the dual energy data sets; an image reconstruction unit connected to the dual energy decomposition unit for generating a reconstructed image for dual energy computed tomography; and a displaying unit operationally connected to the image reconstruction unit for displaying the dual energy computed tomography.

According to a fourth aspect of the current invention, a dual energy computed tomography (CT) system for performing pre-reconstruction decomposition on dual energy data for fast kv-switching acquisition, includes: a fast switching acquisition device for alternating an energy level at an X ray tube between a predetermined high level and a predetermined low level and for acquiring dual energy data sets at substantially 900 total number of projections per rotation (TPPR); a dual energy decomposition unit operationally connected to the fast switching acquisition device for symmetrically matching the dual energy data sets into symmetrically matched pairs of the dual energy data sets and performing pre-reconstruction decomposition on the symmetrically matched pairs of the dual energy data sets; an image reconstruction unit connected to the dual energy decomposition unit for generating a reconstructed image for dual energy computed tomography; and a displaying unit operationally connected to the image reconstruction unit for displaying the dual energy computed tomography.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

FIG. 4 is a diagram illustrating an image processing system for dual energy decomposition according to the current invention.

FIG. 7A is a schematic diagram for illustrating prior art asymmetric decomposition of fast kV-switching dual energy data.

FIG. 7B is a schematic diagram for illustrating symmetric decomposition of fast kV-switching dual energy data according to the current invention.

FIG. 7C is a schematic timing diagram of X-ray voltage as used in FIGS. 7A and 7B.

TABLE 1 summarizes advantages and disadvantages of selected ways to acquire dual energy data sets.

TABLE 2 summarizes the unattenuated average beam energies for the eight different spectra.

TABLE 3 summarizes the image noise in circular regions of interest (ROI) in the water and the liver for both the constant mA and power sinusoidal spectral models using the symmetric and asymmetric view combination techniques in dual energy decomposition.

DETAILED DESCRIPTION OF THE PREFERRED EMBODIMENT(S)

Figure 1:
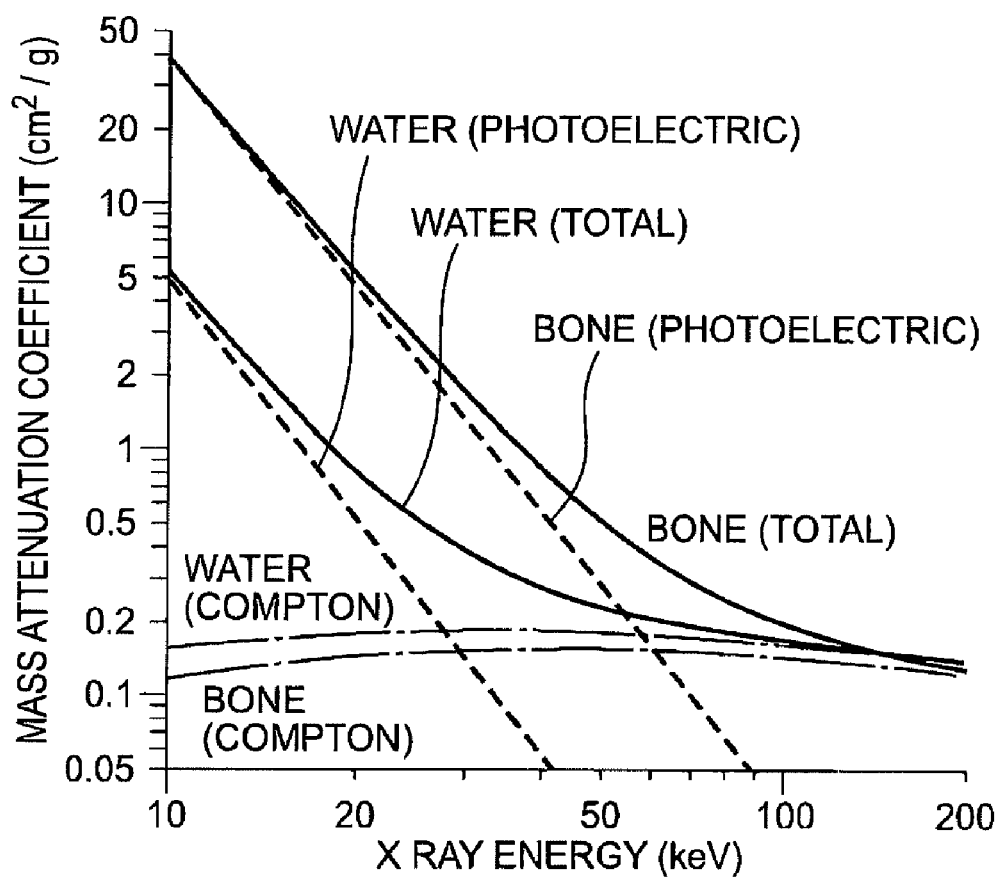
FIG. 1 is a graph depicting prior art information on mass attenuation coefficients as a function of energy in photoelectric absorption and Compton scattering for basis material such as water and bone.
Figure 2A:
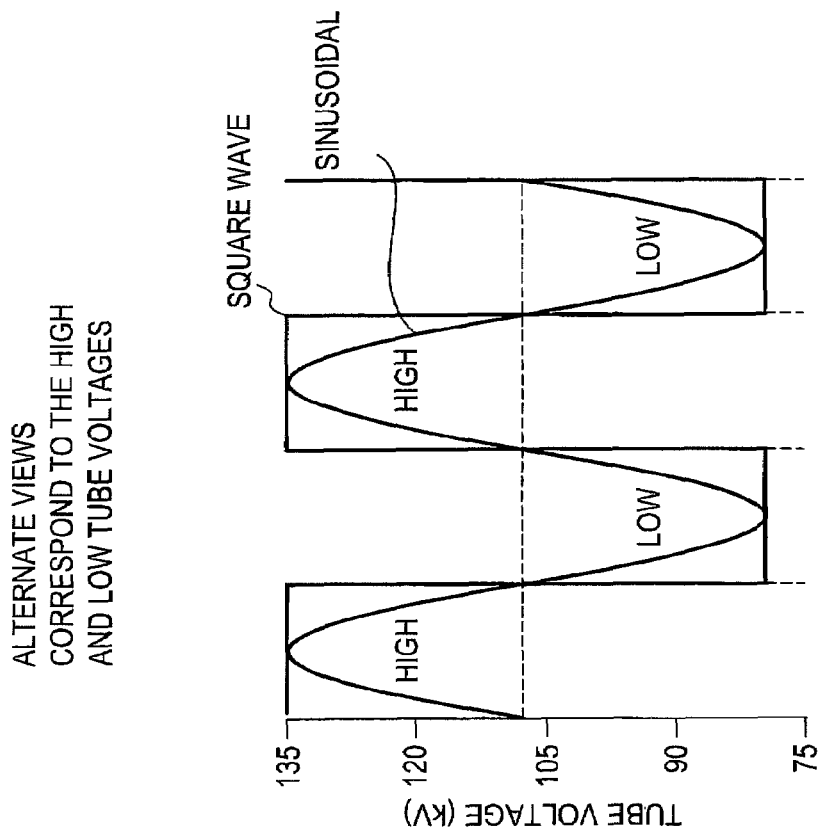
FIG. 2A is a schematic diagram for illustrating a prior art fast kV-switching dual energy data acquisition technique.
Figure 2B:
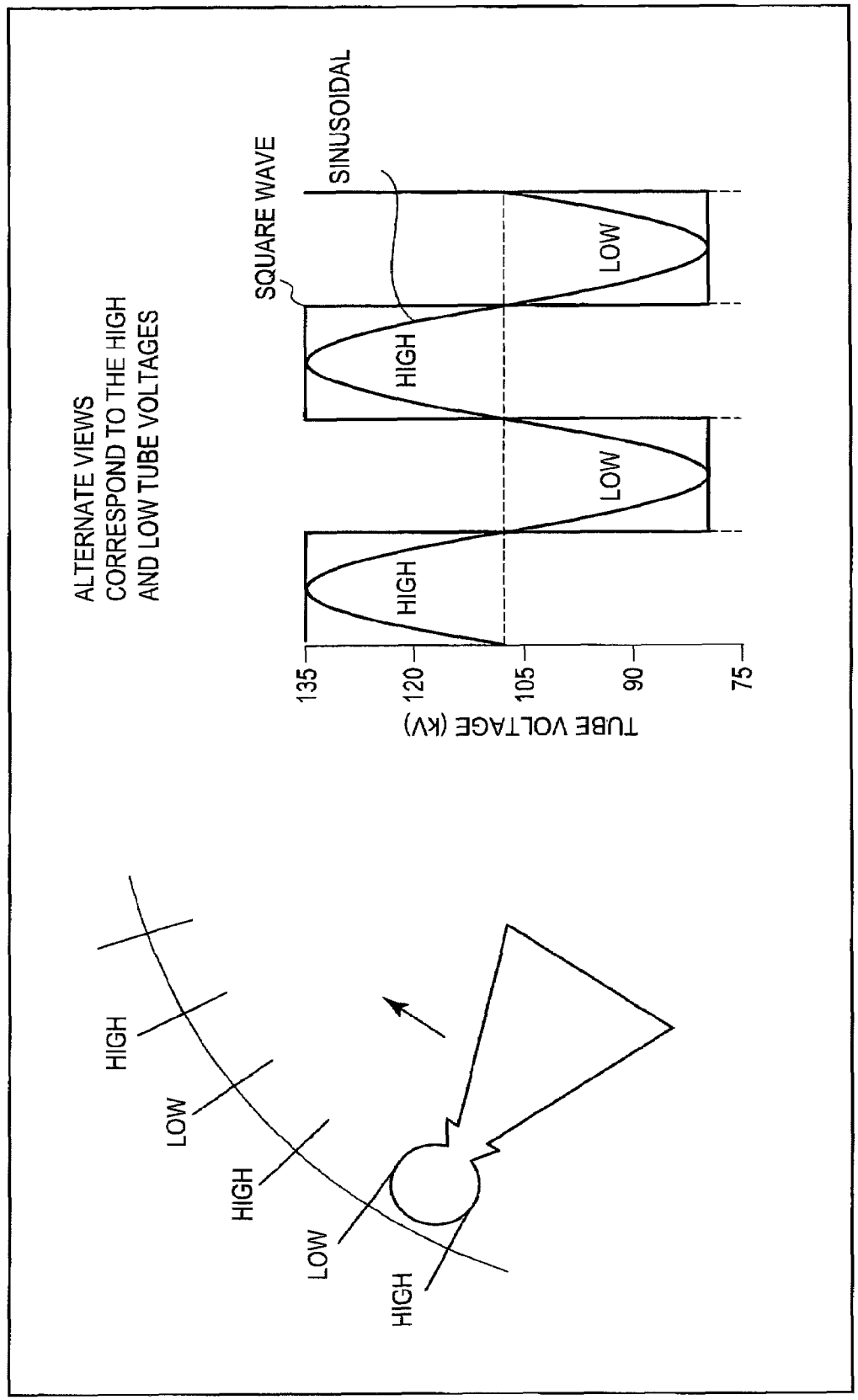
FIG. 2B is a schematic graph for illustrating the high and low tube voltages for a prior art fast kV-switching dual energy data acquisition technique.
Figure 3:
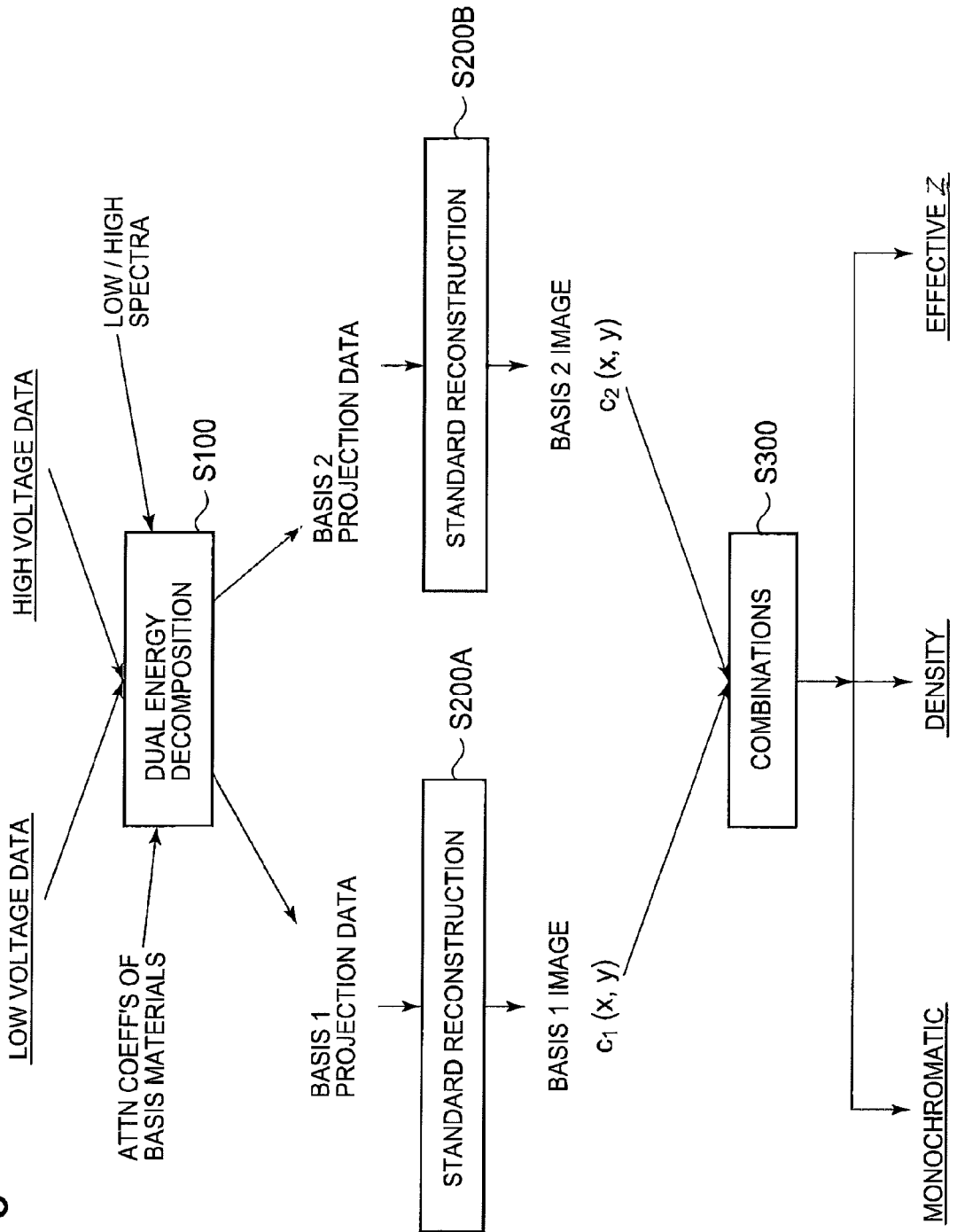
FIG. 3 is a flow chart illustrating image processing of dual energy data sets including dual energy decomposition according to the current invention.

Referring now to the drawings, wherein like reference numerals designate corresponding structures throughout the views, and referring in particular to FIG. 3, a flow chart partially illustrates a preferred method of pre-reconstruction decomposition for fast kV-switching acquisition in dual energy computed tomography according to the current invention. The preferred process receives low voltage data and high voltage data from a predetermined fast kV-switching acquisition step prior to performing pre-reconstruction decomposition for dual energy computed tomography. In a step S100, the preferred process also receives a set of attenuation coefficients for predetermined basis materials and relative photon number for the low/high data in order to process the dual energy data sets. Assuming two basis materials, the preferred process in the step S100 generate basis 1 projection data and basis 2 projection data via the dual energy decomposition based upon the attenuation coefficients and the relative photon number. Furthermore, during the step S100, the dual energy data is symmetrically combined as will be later explained in detail with respect to FIG. 7B. Following the dual energy decomposition step S100, the preferred process generates basis 1 image and basis 2 image respectively from basis 1 projection data and basis 2 projection data through a step S200A and a step S200B with a standard prior art reconstruction technique. Furthermore, the preferred process combines the above generated basis 1 and 2 images in a step S300 and selectively renders a monochromatic image, a density image or an effective Z image to be displayed at a monitor.

Referring to FIG. 4, a schematic diagram partially illustrates a system for a pre-reconstruction decomposition for fast kV-switching acquisition in dual energy computed tomography according to the current invention In general, the preferred embodiment generates low voltage data and high voltage data in a predetermined fast kV-switching acquisition device prior to performing pre-reconstruction decomposition for dual energy computed tomography. The fast kV-switching acquisition device further includes a polychromatic spectra energy source 401 at predetermined energy levels such as 80 kV and 135 kV for radiating a sinusoidal waveform onto a desirable portion of an object 402 and a polychromatic spectra energy sensor 403 for sensing the alternating X-ray that have been projected onto the object 402. The fast kV-switching acquisition device as used in the preferred embodiment includes a prior art energy source and a prior art energy sensor.

Still referring to FIG. 4, the preferred embodiment also includes an image processing unit 400 for processing the dual energy data. In particular, a dual energy data receiving unit 404 receives the dual energy data from the polychromatic spectra energy sensor 403 while a dual energy decomposition unit 405 performs pre-reconstruction decomposition on the received dual energy data for dual energy computed tomography. Furthermore, the dual energy decomposition unit 405 symmetrically combines the dual energy data as will be later explained in detail with respect to FIG. 7B. The dual energy decomposition unit 405 generates projection data based upon attenuation coefficients of basis materials and the known low and high spectra. An image reconstruction unit 406 generates a corresponding image for the projection data before a data combination unit 407 selectively combines the reconstructed images from the image reconstruction unit 406 in order to output a combined reconstructed image 408, which includes a monochromatic image, a density image or an effective Z image. Finally, a display unit of the preferred embodiment displays the outputted reconstructed image 408.

Figure 5A:
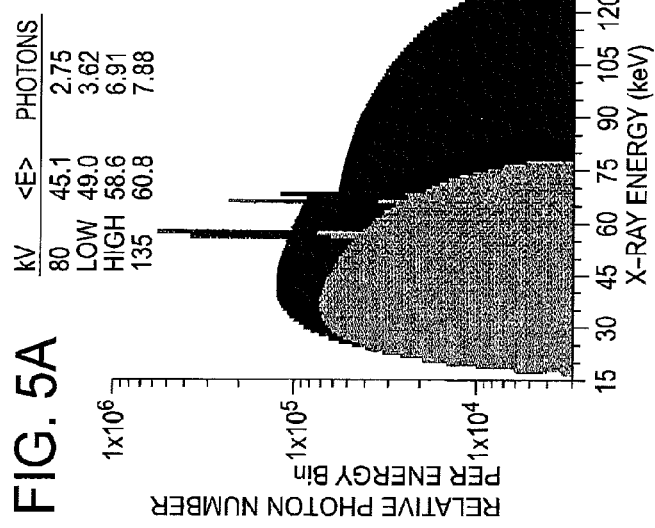
FIGS. 5A and 5B are respectively a graph depicting spectra for a constant mA model and a constant power model.
Figure 5B:
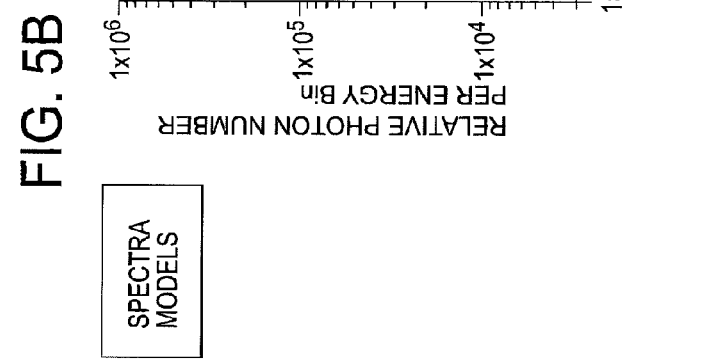

Referring to FIGS. 5A and 5B, spectra data are respectively depicted for a constant mA model and a constant power model in consideration for use in the dual energy decomposition in the above preferred method and system. The spectra are depicted from top to bottom raging 135 kV as illustrated in solid black, sinusoidal high as illustrated in lattice grid, sinusoidal low as illustrated in horizontal lines, and 80 kV as illustrated dotted area. In the constant mA model, the tube current is the same for all tube voltages. In the constant power model, the product of the tube current and tube voltage is fixed for all kV. Although it is technically more feasible to keep the mA constant during the fast kV-switching for the current generation of sub-second rotating gantries, constant power is also offered as a reasonable alternative.

FIGS. 5A and 5B compare the relative tube output as a function of energy for the 135 kV/80 kV square wave example and the high and low spectra for a sinusoidal waveform. In a preferred embodiment, a bow-tie filter and the energy-dependent quantum efficiency of the detector are incorporated in the spectrum models. With the bow-tie filter, the spectral results depend on a channel or an individual x-ray sensor in the detector array. To simplify the simulations, the middle row of the detector array is only considered. For this reason, all simulations and reconstructions use fan-beam rather than cone-beam geometry as well as circular acquisition. Some of the simulations are noiseless and some include Poisson statistics.

Figure 5C:
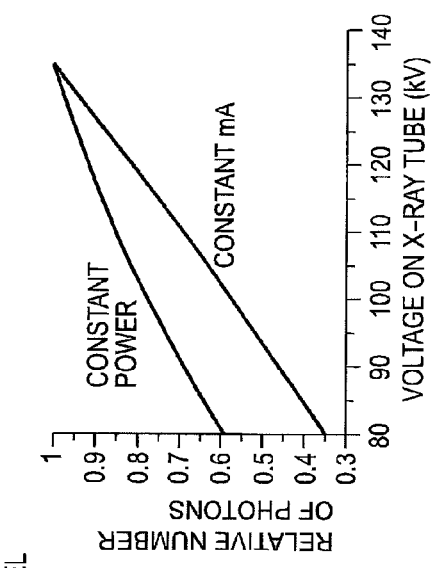
FIG. 5C plots a relative photon count of FIGS. 5A and 5B respectively by the two curves.

The area under the curves in FIGS. 5A and 5B gives a relative photon count as plotted by the two curves in FIG. 5C as a function of kV. That is, a relative number of unattenuated photons from the source is plotted as a function of tube voltage for the constant mA and constant power models. For the sinusoidal waveform, 30 points are used to sample a waveform that oscillates between 80 kV and 135 kV. The simulation of the projection data using the sinusoidal-waveforms include the sub-view angular shift for each sample of waveform. For the dual energy decomposition, the high energy spectrum is the average of the 15 sampled spectra above 107.5 keV, and the low energy spectrum is the average of the 15 spectra below 107.5 keV. The constant power model increases the number of photons especially for the lower energy spectra.

Figure 6:
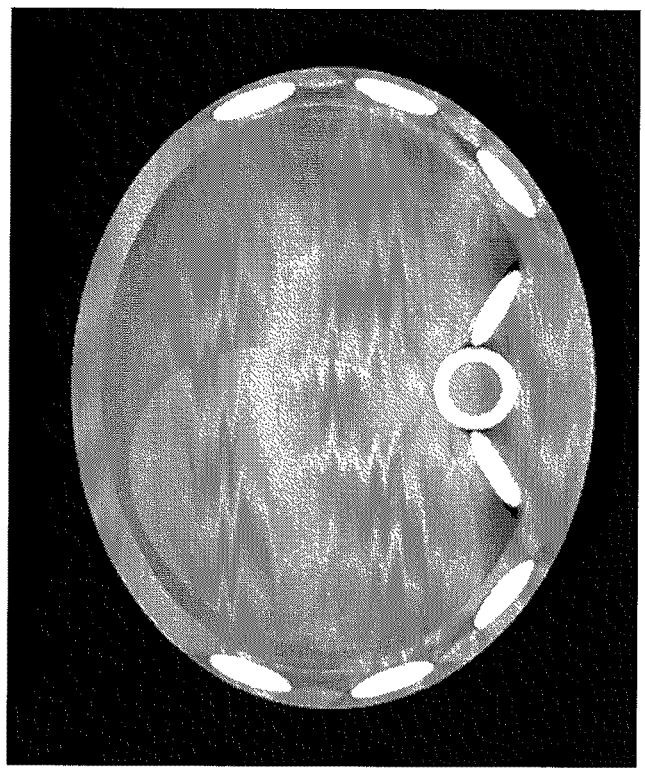
FIG. 6 shows the shading and streak artifacts in the image from an 80 kV noiseless, 3600 total projections per rotation (TPPR) simulation.

Now referring to FIG. 6, the phantom represents a slice of an adult abdomen where the outer ellipse is 320 mm by 260 mm. The outer layer is represented by muscle tissue, while most of the interior is water containing a large ellipse representing liver tissue, but there are nine separate solid bone objects. All of the tissue types have realistic energy behavior and have realistic elemental composition. As shown in FIG. 6, the shading and streak artifacts are seen in the polychromatic reconstruction from an 80 kV noiseless, 3600 total projections per rotation (TPPR) simulation, where data are air calibrated. Since no attempt is made to correct the polychromaticity, the artifacts are resulted. In the following, however, all other images in this specification are generated in monochromatic reconstructions with the above described dual energy decomposition method.

Now referring to FIGS. 7A and 7B, the preferred process and system utilize symmetric view combinations in dual energy decomposition according to the current invention. FIG. 7A is a schematic diagram for illustrating prior art asymmetric viewing combinations in dual energy decomposition of fast kV-switching dual energy data. FIG. 7A shows that dark circles illustrate data associated with views taken at the locations where X-ray is projected at a predetermined high-voltage level such as 135 kV as indicated in a timing diagram of X-ray voltage in FIG. 7C. Similarly, white circles illustrate data associated with views taken at the locations where X-ray is at a predetermined low-voltage level such as 80 kV as indicated in a timing diagram of X-ray voltage in FIG. 7C. In dual energy decomposition, a prior art asymmetric viewing technique combines the high-voltage data and the low-voltage data that is immediately adjacent to the high-voltage data. In other words, in the prior art asymmetric decomposition, the odd projections are from either one of the higher or lower energy spectra while the even projections are the other one of the higher or lower energy spectra, and the neighboring odd and even projections are matched as expressed as follows where the numbers 0 through n+3 each indicate separate but continuously adjacent indicate views or projections:

$\{0,1\}$ $\{2,3\}$ ... $\{n,n+1\}$ $\{n+2,n+3\}$ ...

In the prior art asymmetric viewing technique, since each matched pair is distinct, there is no overlap between the two adjacent combined data. Consequently, the projection lacks a common location. The data domain decomposition suffers from a one-view misregistration. Equally significant is that due to the distinct pairs, given the same number of projections, the total number of total projections per rotation (TPPR) is reduced to one half in the matched pairs before reconstruction.

In contrast, FIG. 7B is a schematic diagram for illustrating symmetric decomposition of fast kV-switching dual energy data according to the current invention. FIG. 7B shows that dark circles illustrate data associated with views taken at the locations where X-ray is projected at a predetermined high-voltage level such as 135 kV as indicated in a timing diagram of X-ray voltage in FIG. 7C. Similarly, white circles illustrate data associated with views taken at the locations where X-ray is at a predetermined low-voltage level such as 80 kV as indicated in a timing diagram of X-ray voltage in FIG. 7C. In dual energy decomposition, a symmetric viewing technique combines the high-voltage data and the low-voltage that is immediately adjacent to the high-voltage data, but the same low-voltage data is matched again with other high-voltage data that is immediately adjacent to the low-voltage data. In other words, in the symmetric decomposition according to the current invention, the odd projections are from either one of the higher or lower energy spectra while the even projections are the other one of the higher or lower energy spectra, and the neighboring odd and even projections are matched as expressed as follows where the numbers 0 through n+2 each indicate separate but continuously adjacent views or projections:

{0,1} {1,2} {2,3} ... {n−1,n} {n,n+1} {n+1,n+2} ...

In the symmetric viewing technique according to the current invention, since each matched pair is not completely distinct, there is some overlap between the two adjacent combined data. Consequently, due to the overlapping data between pairs, the data domain decomposition substantially improves view misregistration. Equally significant is that given the same number of projections as the asymmetric matching, the symmetric matching maintains a number of the TPPR in the matched pairs.

Figures 8A, 8B:
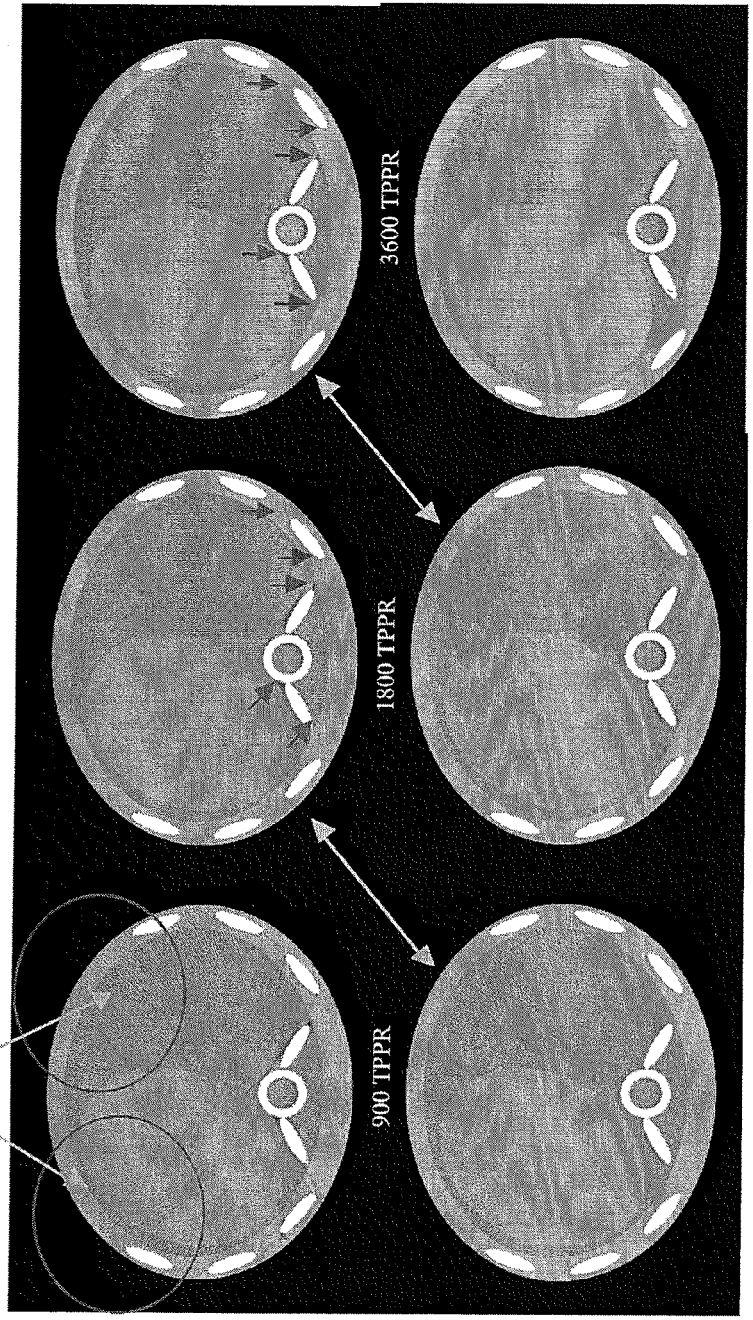
FIG. 8A illustrates monochromatic reconstructions from dual energy data at different number of projections per rotation (TPPR) using a prior art asymmetric matching technique.
FIG. 8B illustrates monochromatic reconstructions from dual energy data at different number of projections per rotation (TPPR) using the symmetric matching technique according to the current invention.

Now referring to FIGS. 8A and 8B, illustrate monochromatic reconstructions from dual energy data at different numbers in total projections per rotation (TPPR) respectively using a prior art asymmetric matching technique and the symmetric matching technique according to the current invention. In particular, referring to FIG. 8A, monochromatic reconstructions at 80 keV are generated using a prior art asymmetric matching technique from dual energy data at 900 TPPR, 1800 TPPR and 3600 TPPR. The dual energy is based upon square-wave at 80 kV and 135 kV with noiseless simulation. Window level and width is 0/300 HU. By the same token, monochromatic reconstructions in FIG. 8B are generated using the symmetric matching technique from dual energy data at 900 TPPR, 1800 TPPR and 3600 TPPR. The dual energy is also based upon square-wave at 80 kV and 135 kV with noiseless simulation. Window level and width is 0/300 HU.

FIG. 8A shows that although the images with noiseless data, the one view mismatch due to the prior art asymmetric viewing technique causes noticeable streaks with 900 TPPR as indicated by ovals. Although not shown clearly with this phantom, the streaks from asymmetric matching have a radial dependence, getting stronger away from the center of the gantry. The streaking appears largely absent in the corresponding image at 1800 TPPR, and it substantially vanishes at 3600 TPPR. On the other hand, as indicated by arrows, other artifacts are seen with 1800 TPPR and 3600 TPPR using the asymmetric combining technique.

In sharp contrast, as shown in bottom row of FIG. 8B, the streaking largely disappears even with 900 TPPR using the symmetric combination technique according to the current invention. In other words, in contrast to the asymmetric combination technique as indicated by double-headed arrows, a number of total projections per rotation (TPPR) is halved using the symmetric combination technique to achieve the same or improved result in reducing the artifacts due to misregistration in data domain decomposition of the dual energy data for the above described fast-kV switching acquisition. Furthermore, there is substantially no difference in image quality in terms of streaking artifacts between the two monochromatic reconstructions at 900 and 1800 TPPR using the symmetric combination technique according to the current invention. Consequently, the symmetric combination technique according to the current invention substantially improves the artifacts at a lower TPPR level than the prior art asymmetric combination technique in data domain decomposition of the dual energy data for the above described fast-kV switching acquisition.

In further detail, using the asymmetric combination technique, the 900 TPPR data result in 450 pairs of dual energy projection data sets with one view misregistration. On the other hand, using the symmetric combination technique, the 900 TPPR data result in 900 pairs of dual energy projection data sets with one view misregistration. In other words, given the same reconstruction algorithm and the same TPPR, the overall image processing time is obviously shorter for the asymmetric combination technique due to the less number of pairs of combined data. On the other hand, also given the same reconstruction algorithm and the same TPPR, the overall image quality is obviously better for the symmetric combination technique due to the more number of pairs of combined data. In summary, in contrast to the asymmetric combination technique, a number of total projections per rotation (TPPR) is halved using the symmetric combination technique to achieve the same or even better results to substantially reduce the artifacts due to misregistration in the dual energy data for the above described fast-kV switching acquisition. Consequently, due to the symmetric viewing technique in pre-construction decomposition, a quality image substantially free from the artifacts is available from dual energy data in fast kV switching acquisition in a cost-effective manner.

TABLE 2 summarizes the unattenuated average beam energies for the eight different spectra. For the square wave, the energy separation is 15.7 keV between 135 kV and 80 kV. On the other hand, for the sinusoidal waveform, the energy separation between the high (100 kV) and the low (80 kV) is reduced to 9.6 keV for the constant mA model while the energy separation between the high (135 kV) and the low (120 kV) is reduced to 9.7 keV for the constant power model. In fast kV-switching, since only sinusoidal waveforms are generally practical and might not give enough energy separation between the low and high data sets, the high energy spectrum is fixed at 135 kV and combined with low energy data at 80 kV, 100 kV and 120 kV in the preferred embodiment according to the current invention.

TABLE 2

| Square Wave | | Sinusoidal Waveform | |
| --- | --- | --- | --- |
| kV | <E> | kV | <E> |
| 80 | 45.1 | Low: Constant Power | 48.7 |
| 100 | 51.6 | High: Constant Power | 58.4 |
| 120 | 57.1 | Low: Constant mA | 49.0 |
| 135 | 60.8 | High: Constant mA | 58.6 |

Figure 9:
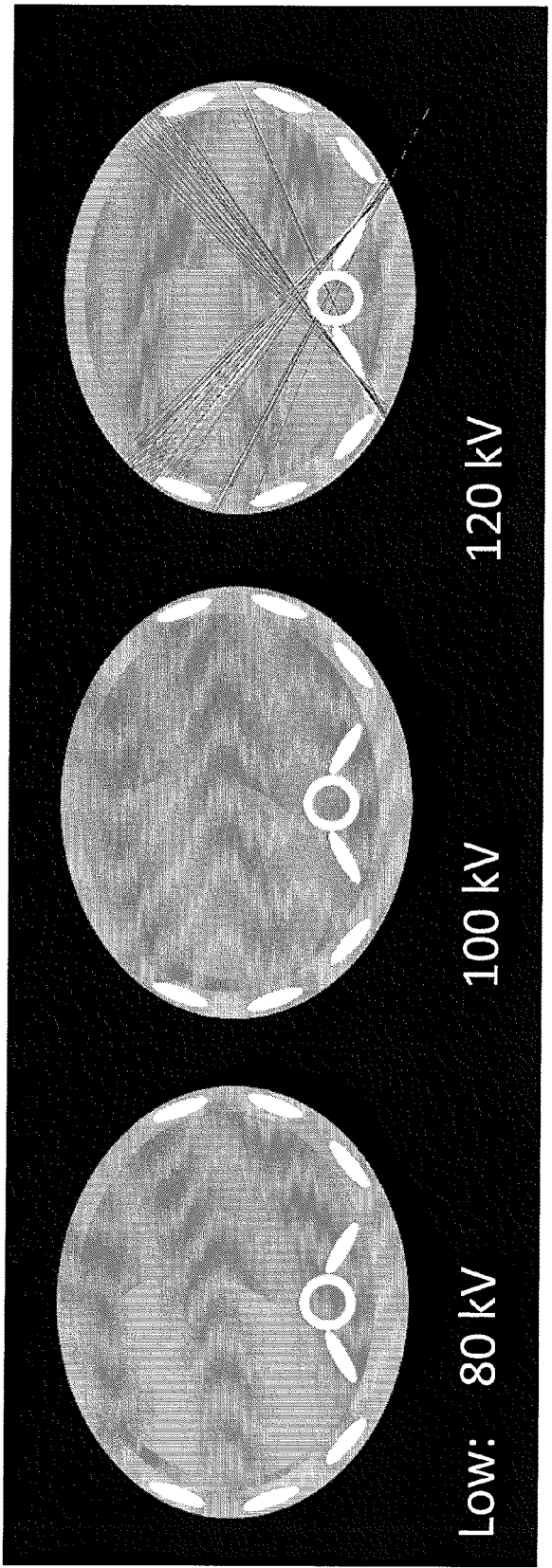
FIG. 9 shows monochromatic reconstructions from square-waveform dual energy waveform with the high energy spectrum fixed at 135 kV while the low energy spectrum is changed from 80 kV to 100 kV and 120 kV.

FIG. 9 shows monochromatic reconstructions from square-waveform dual energy waveform with the high energy spectrum fixed at 135 kV while the low energy spectrum is changed from 80 kV, 100 kV to 120 kV. Although the dual energy decomposition is stable at 80 kV and 100 kV, it breaks down at 120 kV and results in undesirable artifacts. As derived from the average energies in TABLE 2, the difference between the 135 kV and 120 kV spectra is only 3.7 keV, while the 135 kV and 100 kV difference was 9.2 keV. With the two sinusoidal models, the difference between the high and low spectra is 9.6 or 9.7 keV.

Figure 10:
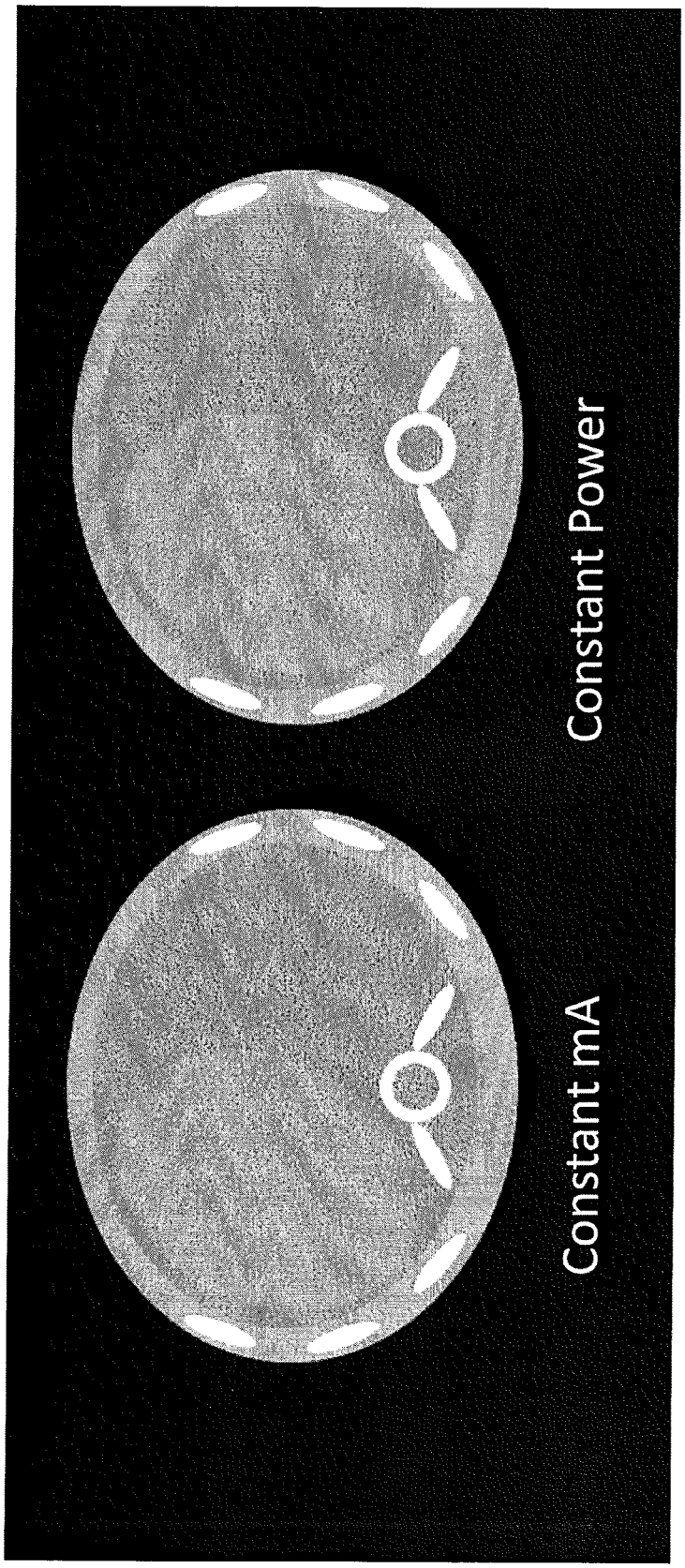
FIG. 10 shows the sinusoidal-waveform results with both constant mA and constant power models.

In this regard, FIG. 10 shows monochromatic reconstructions at 80 keV using the sinusoidal-waveform with the constant mA model in the left and the constant power model in the right both at 1800 TPPR with the symmetric matching technique. The image quality is good as expected because the spectra differences are greater than that between 135 kV and 100 kV square-wave spectral pair, which showed good image quality.

TABLE 3 summarizes the image noise in circular regions-of-interest (ROI) in the water and the liver for both the constant mA and power sinusoidal spectral models using the symmetric and asymmetric view combination techniques in dual energy decomposition. Measurements have been made in the 80 keV monochromatic reconstructions Mean and standard deviation are calculated for a circular region-of-interest within a 45-pixel radius centered in the water and liver regions for the constant mA and constant power spectral models using both symmetric and asymmetric view matching in the dual energy processing. The noise reduction for the symmetric view matching is nearly 10% in the water ROI and 6.5% in the liver ROI. The noise reduction for using constant power rather than constant mA is 5.5% in the water ROI and 4.8% in the liver ROI

TABLE 3

| Spectral Model | ROI | Symmetric | Asymmetric |
|---|---|---|---|
| Constant mA | Water | 0.7 ± 50.9 | 0.8 ± 55.8 |
| | Liver | 29.3 ± 54.1 | 29.1 ± 57.8 |
| Constant Power | Water | 0.4 ± 48.1 | 0.5 ± 53.4 |
| | Liver | 29.4 ± 51.5 | 29.3 ± 55.1 |

Figure 12:
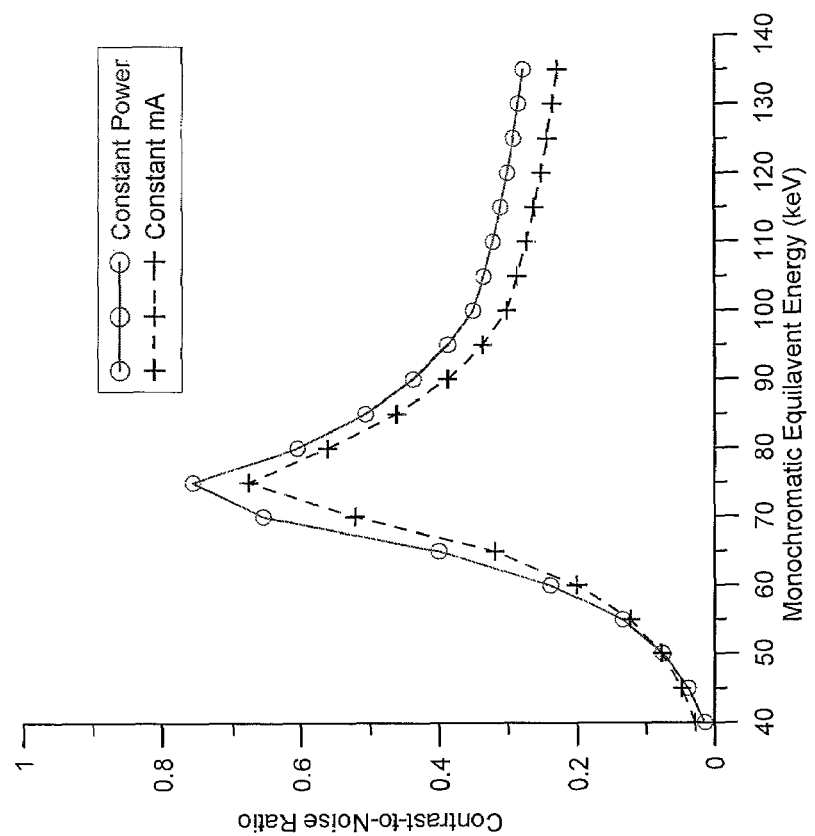
FIG. 12 illustrates the contrast-to-noise ratio (CNR) by taking the difference in the liver and water means.
Figure 11:
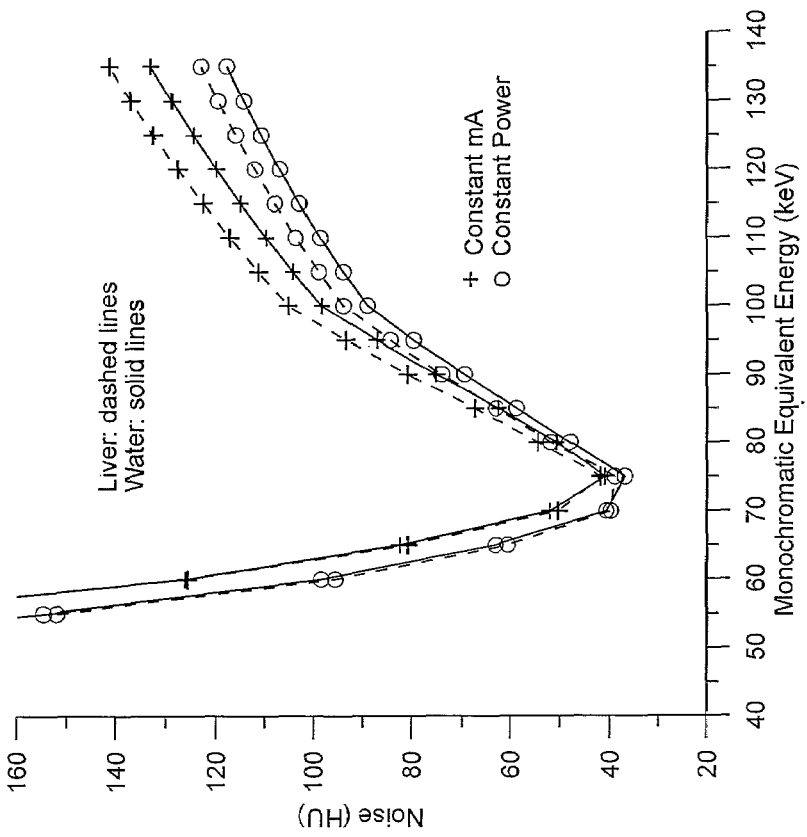
FIG. 11 illustrates the noise as a function of monochromatic keV for the dual energy processed image with symmetric matching.

Referring to FIG. 11, the noise is shown as a function of monochromatic equivalent energy for the dual energy processed image with symmetric matching as related to the above Eqn. (4). The noise reduction is strongest at 75 keV and has a surprisingly narrow peak. It remains to be seen in the future study to better understand the dependence of the peak shape on the relative noise contributions from the high and low data sets. Consequently, when the contrast-to-noise ratio (CNR) is formed by taking the contrast as the difference in the liver and water means, it has a corresponding sharp peak at 75 keV as illustrated in FIG. 12. The CNR improves by 11.9% when using the constant power model over the constant mA model at the peak.

Figure 13:
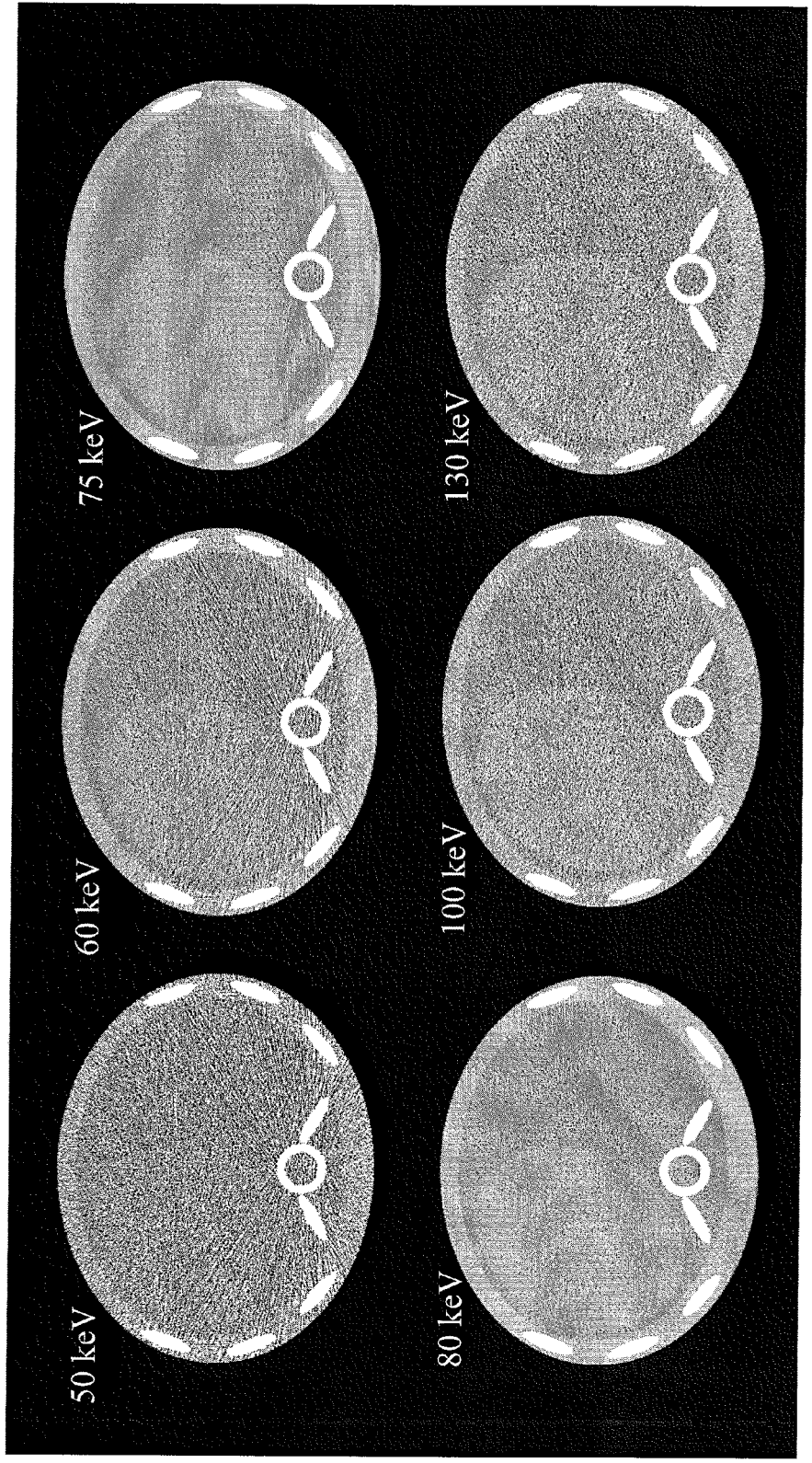
FIG. 13 is a panel of exemplary various monochromatic images with different monochromatic equivalent energies using the constant power spectral model and symmetric view matching.

Referring to FIG. 13, a panel of various exemplary monochromatic images is shown with different monochromatic equivalent energies using the constant power spectral model and symmetric view matching. Window/level is 0/300. As being pushed towards lower monochromatic energies, the resultant image replies too much on the low energy scan A problem arises with a low photon count for some ray-sums to result in the observed streaks in the top row of FIG. 13. No effort was made to adaptively smooth the noise in the low count regions. Similarly, if pusing towards higher energies, the resultant image replies too much on the high energy scan.

Although a sinusoidal waveform for fast kV-switching is not as desirable as a square wave, it nevertheless gives adequate energy separation between the high and low spectra. Image quality is improved with symmetric view matching, both from eliminating the streaks from the one view mis-registration and for noise reduction. The constant power model for the sinusoidal waveform helps reduce noise but is not essential. The monochromatic image at 75 keV gives the best contrast-to-noise performance, although some evidence of photon starvation streaks from the low energy data are present that are gone for images at 80 keV and above. Increasing the number of low energy photons, if technically possible beyond the constant power model, would help. Dual energy scanning might be problematic for patients with high attenuation because of the need for a low energy scan, which has limited penetration. Adaptive filtering of the low signals might help.

Figure 14:
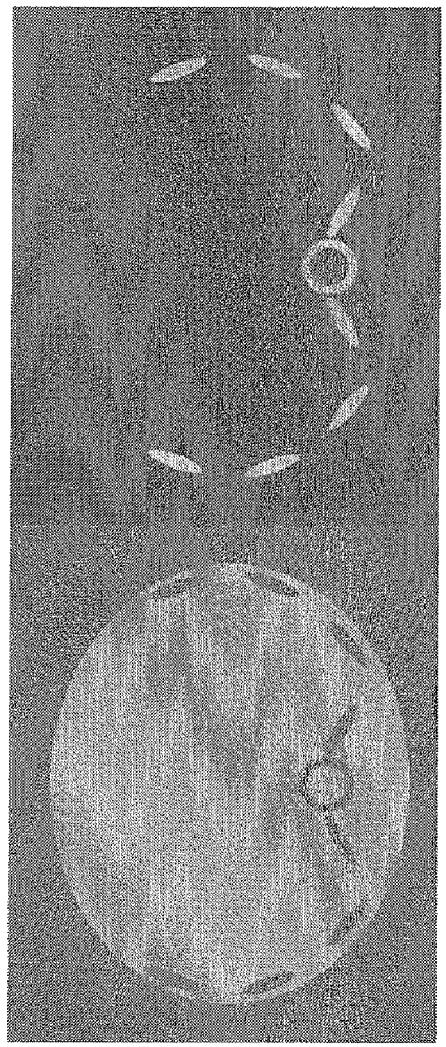
FIG. 14 is a panel of exemplary images using basis functions for water and bone.

All the monochromatic images are free of beam hardening artifacts. As shown in Eqn. 4, the monochromatic images are weighted sums of the reconstructions for the basis materials (water and bone in this study, see FIG. 14), where the weights are the linear attenuation coefficients of the basis functions at the monochromatic energy of interest. Evidently, a monochromatic energy of 75 keV gives the best combination of information from the high and low energy scan for the two sinusoidal spectral models.

Figure 15:
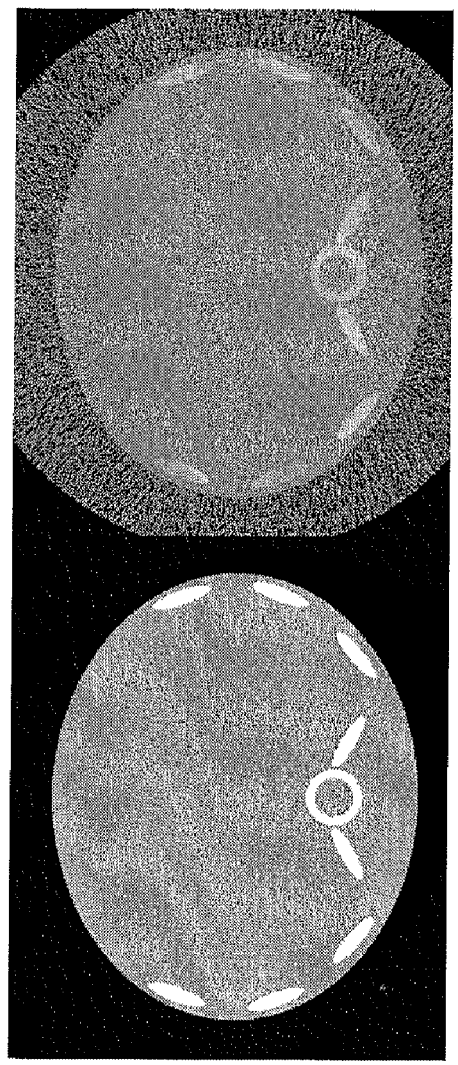
FIG. 15 presents images for the density and atomic number maps for the simulation.

FIG. 15 presents the density and atomic number maps for the simulation. The differences between liver and water tissue are nearly entirely due to density differences. Hence, in this imaging task, CNR variation as a function of monochromatic energy is mostly a function of the noise dependence, not the contrast difference of the two tissues.

It is to be understood, however, that even though numerous characteristics and advantages of the present invention have been set forth in the foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

What is claimed is:

1. A method of processing pre-reconstruction decomposition for fast kv-switching acquisition in dual energy computed tomography (CT), comprising the steps of:
    switching an X ray tube between a predetermined high energy level and a predetermined low energy level at a predetermined frequency;
    acquiring dual energy data sets at a predetermined total number of projections per rotation (TPPR);
    symmetrically matching the dual energy data sets into symmetrically matched pairs of the dual energy data sets, the dual energy data sets including immediately neighboring projections indicated by 0 through n+2, the neighboring projections being alternately acquired at the predetermined high energy level and the predetermined low energy level, wherein the symmetrically matching step includes the symmetrically matched pairs of the projections as being expressed as {0,1} {1,2} {2,3} . . . {n−1,n} {n,n+1}{n+1,n+2}, wherein pairs of the numbers is in the { }'s indicate the above defined immediately neighboring projections;
    performing pre-reconstruction decomposition on the symmetrically matched pairs of the dual energy data sets to generate a dual energy computed tomography; and
    displaying the dual energy computed tomography.

2. The method of processing pre-reconstruction decomposition for fast kv-switching acquisition in dual energy computed tomography according to claim 1, wherein the predetermined total number of projections per rotation (TPPR) is at the most 900 TPPR.

3. The method of processing pre-reconstruction decomposition for fast kv-switching acquisition in dual energy computed tomography according to claim 1, wherein the predetermined total number of projections per rotation (TPPR) is between 900 TPPR and 1800 TPPR.

4. The method of processing pre-reconstruction decomposition for fast kv-switching acquisition in dual energy computed tomography according to claim 1, wherein the predetermined total number of projections per rotation (TPPR) is between 900 TPPR and 3600 TPPR.

5. A method of processing pre-reconstruction decomposition for fast kv-switching acquisition in dual energy computed tomography (CT), comprising the steps of:
   switching an X ray tube between a predetermined high energy level and a predetermined low energy level at a predetermined frequency;
   acquiring dual energy data sets at a predetermined number of projections per rotation (TPPR);
   symmetrically matching the dual energy data sets into symmetrically matched pairs of the dual energy data sets, the dual energy data sets including immediately neighboring projections indicated by 0 through n+2, the neighboring projections being alternately acquired at the predetermined high energy level and the predetermined low energy level, wherein the symmetrically matching step includes the symmetrically matched pairs of the projections as being expressed as $\{0,1\}$ $\{1,2\}$ $\{2,3\}$ ... $\{n-1,n\}$ $\{n,n+1\}$ $\{n+1,n+2\}$, wherein pairs of the numbers is in the { }'s indicate the above defined immediately neighboring projections;
   performing pre-reconstruction decomposition on the symmetrically matched pairs of the dual energy data sets to generate a dual energy computed tomography; and
   displaying the dual energy computed tomography.

6. The method of processing pre-reconstruction decomposition for fast kv-switching acquisition in dual energy computed tomography according to claim 5, wherein the predetermined total number of projections per rotation (TPPR) is at the most 900 TPPR.

7. The method of processing pre-reconstruction decomposition for fast kv-switching acquisition in dual energy computed tomography according to claim 5, wherein the predetermined total number of projections per rotation (TPPR) is between 900 TPPR and 1800 TPPR.

8. The method of processing pre-reconstruction decomposition for fast kv-switching acquisition in dual energy computed tomography according to claim 5, wherein the predetermined total number of projections per rotation (TPPR) is between 900 TPPR and 3600 TPPR.

9. A dual energy computed tomography (CT) system configured to perform pre-reconstruction decomposition on dual energy data for fast kv-switching acquisition, comprising:
   fast switching acquisition device configured to alternate an energy level at an X ray tube between a predetermined high level and a predetermined low level and for acquiring dual energy data sets at a predetermined total number of projections per rotation (TPPR) at a predetermined frequency;
   a dual energy decomposition unit operationally connected to said fast switching acquisition device and configured to symmetrically match the dual energy data sets into symmetrically matched pairs of the dual energy data sets and performing pre-reconstruction decomposition on the symmetrically matched pairs of the dual energy data sets, the dual energy data sets including immediately neighboring projections indicated by 0 through n+2, the neighboring projections being alternately acquired at the predetermined high energy level and the predetermined low energy level, wherein the symmetrically matching step includes the symmetrically matched pairs of the projections as being expressed as $\{0,1\}$ $\{1,2\}$ $\{2,3\}$ ... $\{n-1,n\}$ $\{n,n+1\}$ $\{n+1,n+2\}$, wherein pairs of the numbers is in the { }'s indicate the above defined immediately neighboring projections;
   an image reconstruction unit connected to said dual energy decomposition unit and configured to generate a reconstructed image for dual energy computed tomography from the decomposition of the symmetrically matched pairs of dual energy data sets; and
   a displaying unit operationally connected to said image reconstruction unit and configured to display the reconstructed image.

10. The dual energy computed tomography (CT) system configured to perform pre-reconstruction decomposition according to claim 9, wherein the predetermined total number of projections per rotation (TPPR) is at the most 900 TPPR.

11. The dual energy computed tomography (CT) system configured to perform pre-reconstruction decomposition according to claim 9, wherein the predetermined total number of projections per rotation (TPPR) is between 900 TPPR and 1800 TPPR.

12. The dual energy computed tomography (CT) system configured to perform pre-reconstruction decomposition according to claim 9, wherein the predetermined total number of projections per rotation (TPPR) is between 900 TPPR and 3600 TPPR.

13. A dual energy computed tomography (CT) system configured to perform pre-reconstruction decomposition on dual energy data for fast kv-switching acquisition, comprising:
   fast switching acquisition device configured to alternate an energy level at an X ray tube between a predetermined high level and a predetermined low level and for acquiring dual energy data sets at predetermined number of projections per rotation (TPPR) at a predetermined frequency;
   a dual energy decomposition unit operationally connected to said fast switching acquisition device and configured to symmetrically match the dual energy data sets into symmetrically matched pairs of the dual energy data sets and performing pre-reconstruction decomposition on the symmetrically matched pairs of the dual energy data sets, the dual energy data sets including immediately neighboring projections indicated by 0 through n+2, the neighboring projections being alternately acquired at the predetermined high energy level and the predetermined low energy level, wherein the symmetrically matching step includes the symmetrically matched pairs of the projections as being expressed as $\{0,1\}$ $\{1,2\}$ $\{2,3\}$ ... $\{n-1,n\}$ $\{n,n+1\}$ $\{n+1,n+2\}$, wherein pairs of the numbers is in the { }'s indicate the above defined immediately neighboring projections;
   an image reconstruction unit connected to said dual energy decomposition unit and configured to generate a reconstructed image for dual energy computed tomography from the decomposition of the symmetrically matched pairs of dual energy data sets; and
   a displaying unit operationally connected to said image reconstruction unit and configured to display the reconstructed image.

14. The dual energy computed tomography (CT) system configured to perform pre-reconstruction decomposition according to claim 13, wherein the predetermined total number of projections per rotation (TPPR) is at the most 900 TPPR.

15. The dual energy computed tomography (CT) system configured to perform pre-reconstruction decomposition according to claim 13, wherein the predetermined total number of projections per rotation (TPPR) is between 900 TPPR and 1800 TPPR.

16. The dual energy computed tomography (CT) system configured to perform pre-reconstruction decomposition according to claim 13, wherein the predetermined total number of projections per rotation (TPPR) is between 900 TPPR and 3600 TPPR.

* * * * *